United States Patent [19]

Warren, III et al.

[11] Patent Number: 4,789,525
[45] Date of Patent: Dec. 6, 1988

[54] ANALYTICAL METHOD AND MULTILAYER ELEMENT FOR TOTAL IONIC IRON DETERMINATION

[75] Inventors: Harold C. Warren, III, Rush; John C. Mauck, Rochester, both of N.Y.

[73] Assignee: Eastman Kodak Company, Rochester, N.Y.

[21] Appl. No.: 64,639

[22] Filed: Jun. 22, 1987

[51] Int. Cl.$^4$ .................... G01N 21/75; G01N 33/20
[52] U.S. Cl. ........................... 422/56; 436/74; 436/84
[58] Field of Search ............... 422/56, 57, 58, 61, 422/86, 88; 436/74, 84, 170

[56] References Cited

U.S. PATENT DOCUMENTS

| | | | |
|---|---|---|---|
| 3,537,822 | 11/1970 | O'Malley | 436/74 |
| 4,214,968 | 7/1980 | Battaglia et al. | 204/418 |
| 4,303,408 | 12/1981 | Kim et al. | 422/56 |
| 4,357,412 | 11/1982 | Anderson et al. | 430/233 |
| 4,649,123 | 3/1987 | Charlton et al. | 436/170 |
| 4,735,904 | 4/1988 | Starr | 422/61 |

OTHER PUBLICATIONS

"A Multilayer Element for Determining Hemoglobin in Whole Blood: Principles and Analytical Performance", Burdick et al., Clinical Chemistry, 32/10, 1953–1955 (1986).

"Water-Soluble Pyridylazoaniline Reagents for the Spectrophotometric Determination of Metals", Horiguchi et al., Analytica Chemica Acta, 151 (1983) 457–463.

"Extraction-Spectrophotometric Determination of Iron with 2-[2-(3,5-Dibromopyridyl)Azo]-5-Dimethylaminobenzoic Acid", Katami et al., Analyst, Feb. 1984, vol. 109, 159–162.

"An Auto Analyzer Procedure for Serum Iron and Total Iron-Binding Capacity, With Use of Ferrozine", Yee et al., Clinical Chemistry, vol. 17, No. 9, (1971) 950–953.

Primary Examiner—Barry S. Richman
Assistant Examiner—Lyle Alfandary Alexander
Attorney, Agent, or Firm—John R. Everett

[57] ABSTRACT

A dry multilayer analytical element for determination of total ionic iron is disclosed. The element includes a dye which complexes with $Fe^{+2}$. The dye has the structure

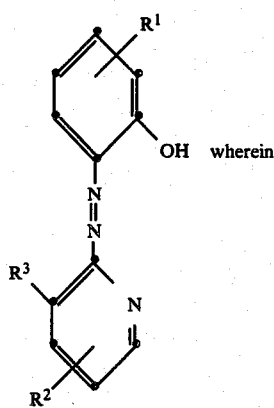

wherein $R^1$ represents an electron donating group; or $R^1$, together with the carbon to which it is attached, represents sufficient atoms to form a cyclic electron donating group fused to the phenyl group to which $R^1$ is attached;

$R^2$ represents an electron withdrawing group; and $R^3$ represents H, Cl, F, Br or $OR^4$ wherein $R^4$ represents a hydrocarbon having from 1 to 20 carbon atoms.

5 Claims, No Drawings

ANALYTICAL METHOD AND MULTILAYER ELEMENT FOR TOTAL IONIC IRON DETERMINATION

FIELD OF THE INVENTION

The present invention relates to a multilayer analytical element for determining total ionic iron in aqueous liquids.

BACKGROUND OF THE INVENTION

Methods for assaying ferrous ion in aqueous liquids such as biological liquids (blood, serum and urine) are known. Such assays are carried out on human serum for the purpose of diagnosing conditions such as anemia, liver disorders and lead poisoning. It is also of interest, for example, to analyze the ferrous ion content in boiler water in steam electric power generating plants. Known methods for ferrous ion determination are generally referred to as wet methods. The reagents involved are first dissolved or suspended in a liquid aqueous vehicle. The resulting aqueous reagents are mixed together and then the ferrous ion measurement is made colorimetrically.

None of the known wet methods for ferrous ion determination have been adapted for use in so-called dry methods. Dry chemical methods have reference to chemical methods which are performed using reagent compositions incorporated in various substantially "dry-to-the-touch" elements. Examples of such elements include "dip and read" test strips and multi-zone analytical test elements. The latter elements are disclosed for example, in U.S. Pat. No. 4,132,528. Also, some of the most effective wet methods for ferrous ion determination are not adaptable to dry chemical techniques because of insufficient sensitivity due to the low extinction coefficients of the ferrous ion-dye complex developed by the method; (2) lack of selectivity from interfering metal cations such as cupric ($Cu^{+2}$) and zinc ($Zn^{+2}$) cations and (3) insufficient rate of metallization at the usual operating pH's of about 4 to 5 necessary to dissociate ferric ion from transferrin in serum assays.

SUMMARY OF THE INVENTION

The present invention provides a multilayer analytical element comprising a support coated in the following order top down to the support;

(a) a spreading layer; and
(b) a reducing layer comprising a reducing agent for $Fe^{+3}$; and
(c) a reagent layer comprising
  (i) a coupler solvent selected from the group consisting of dioctyl phenyl phosphonate and diethyl lauramide;
  (ii) a composition of sufficient concentration to maintain a pH in the range of 4 to 5 when the reagent layer is contacted with an aqueous fluid and
  (iii) a dye having the structure

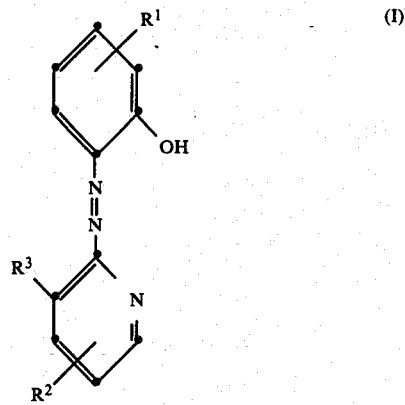

in which $R^1$ represents an electron donating group such as hydroxy or a dialkylamine wherein the alkyl groups include methyl, ethyl, propyl, decyl or palmityl; or, together with the carbon atom to which it is attached, $R^1$ represents sufficient atoms to form a cyclic electron donating group fused to the phenyl group to which $R^1$ is attached;

$R^2$ represents an electron withdrawing group such as

—$SO_2NH_2$,

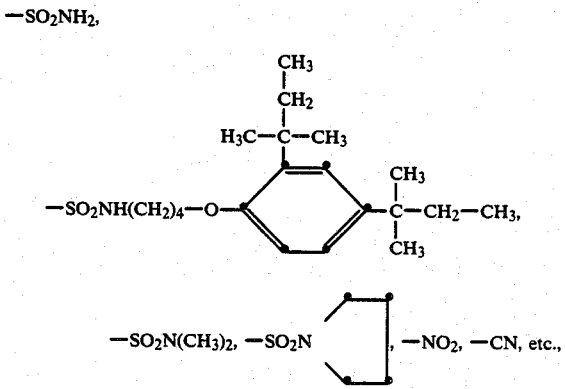

and $R^3$ represents H, Cl, F, Br or $OR^4$ wherein $R^4$ represents a hydrocarbon group having from 1 to 20 carbon atoms such as methyl, phenyl, stryl, palmityl, etc.;

The present invention represents an unexpected improvement over the prior art. The colored $Fe^{+2}$ complex is easily measured because of its high extinction coefficient. The complex is sufficiently formed within five minutes to allow effective measurement of the $Fe^{+2}$ concentration colorimetrically. This rate of complex formation is a substantial improvement over the prior art dyes disclosed for metal ion determination in *Analytical Chimica Arta*, 151 (1983) 457–463.

The coupler solvent used herein minimizes formation of any $Zn^{+2}$ or $Cu^{+2}$ dye complexes.

DETAILED DESCRIPTION OF THE INVENTION

The element of this invention can be used to assay total ionic iron qualitatively and quantitatively in biological fluids in animals or humans, but preferably of humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

Elements of the invention can be configured in a variety of forms, including elongated tapes of any desired width, sheets, slides or chips.

The elements can be used in manual or automated assay techniques. In general, in using the elements, total ionic iron determination is made by taking the element from a supply roll, chip packet or other source and physically contacting it with a sample (for example, up to 200 μl) of the liquid to be tested so that the sample and reagents within the element become mixed. Such contact can be accomplished in any suitable manner, for example, by dipping or immersing the element into the sample or, preferably, by spotting the element by hand or machine with a drop of the sample with a suitable dispensing means.

After sample application, the element is incubated, for a period of up to 5 minutes, to facilitate color development. By incubation, we simply mean that the reagents are maintained in contact with each other for a period of up to 5 minutes before color measurements are made.

The coupler solvent is essential to the invention. It minimizes zinc ion and copper ion interference in the ferrous ion assay method of this invention by preventing the dye from complexing to these metal ions. The useful coupler solvents are dioctyl phenyl phosphonate and diethyl lauramide from 0.5 to 8.0 g/m² or coupler solvent will be useful.

The dyes which are useful in this invention can be made by the methods disclosed in U.S. Pat. No. 4,357,412, particularly example 2 thereof. Representative useful dyes have the structure:

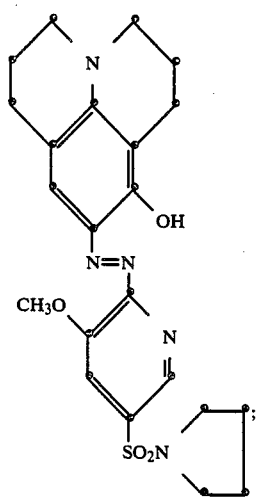

-continued

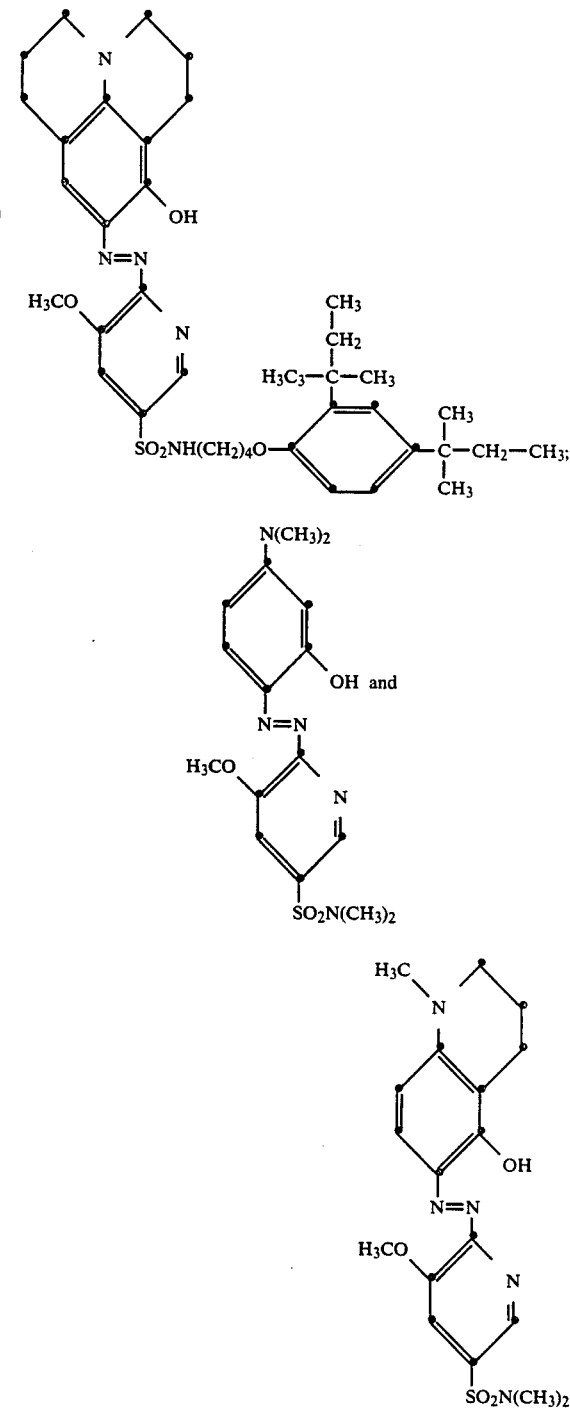

The dry analytical elements of this invention are multilayered. At least one of the layers is preferably a porous spreading zone. The other layers include a reagent layer and a reduction layer. The reagent layer includes a barrier zone and a reagent zone. All of the foregoing layers are coated on a support. The layers are generally in fluid contact with each other, meaning that fluids, reagents and reaction products (for example, color dyes) can pass or be transported between superposed regions of adjacent zones. In other words, when the element is contacted with fluid, all reagents of the analytical composition of this invention become mixed and can readily move within the element as a composition. Preferably, each layer is a separately coated layer, although two or more zones can be separate areas in a single layer of the element. Besides the references noted above, suitable element components are described also. For example, in U.S. Pat. Nos. 4,042,335 (issued Aug. 16, 1977 to Clément), 4,132,528 (issued Jan. 2, 1979 to Eikenberry et al), and 4,144,306 (issued Mar. 13, 1979 to Figueras).

The multilayer element of this invention requires only one reagent layer. The reagent layer can be divided into two zones. The first zone is a reagent zone. It comprises the dye and coupler solvent. The second zone is a barrier zone and comprises gelatin and a hardener. It is desirable to separate these two zones because of potential dye and coupler solvent migration. The dyes are soluble in the selected coupler solvents. When the gelatin is hardened, the coupler solvent and the dye cannot diffuse into the spreading layer. Also, large molecules, such as hemoglobin, stay in the spreading layer and thus cannot become spectral interferants.

Useful spreading layers can be prepared using fibrous materials, either mixed with a suitable binder material or woven into a fabric, as described in U.S. Pat. No. 4,292,272 (issued Sept. 29, 1981 to Kitajima et al), polymeric compositions or particulate materials, for example a blush polymer such as disclosed in U.S. Pat. No. 3,992,158, beads bound together with or without binding adhesives, as described in U.S. Pat. Nos. 4,258,001 (issued Mar. 24, 1981 to Pierce et al) and 4,430,436 (issued Feb. 7, 1984 to Koyama et al) and Japanese Patent Publication No. 57(1982)-101760. Since the sample is generally applied directly to the spreading layer, it is desirable that the spreading layer be isotropically porous, meaning that the porosity is the same in each direction in the layer as caused by interconnected spaces or pores between particles, fibers or polymeric strands.

The reducing layer is present to reduce any $Fe^{+3}$ to $Fe^{+2}$. Iron can exist in two ionic states. These are ferrous ($Fe^{+2}$) and ferric ($Fe^{+3}$). These forms exist in equilibrium. For example in serum, a portion of the iron exists as $Fe^{+3}$ complexed to a protein called transferrin. The dyes of Formula I complex only ferrous ($Fe^{+2}$) iron at pH 4-5. Therefore any $Fe^{+3}$ in the sample must be reduced to $Fe^{+2}$ before it can react with the dye. Any appropriate reducing agent can be used. Examples are hydroxlamine.HCl, para-methylamino sulfate, ascorbic acid and ascorbyl palmitate. The inclusion of reducing agents to reduce $Fe^{+3}$ to $Fe^{+2}$ is well known in the art. In a preferred embodiment the reducing agent is in a layer of the element.

The layers can be coated on transparent supports such as polyethylene terephthalate. Other supports are well known in this art. From the top down to the support, the element comprises the spreading layer, the reducing layer and the reagent layer.

Sometimes it is advisable to use a material such as neocuproine to chelate any endogenous copper in the test liquid. This reagent may be located in the reducing layer or the reagent layer. This is necessary in spite of the presence of a coupler solvent because of limited solubility of the coupler solvents.

The elements of this invention can also contain one or more other addenda commonly put in the elements for various manufacturing or operational advantages. Such addenda include surfactants, buffers, solvents, hardeners and other materials known in the art.

The method and elements of this invention were evaluated for effectiveness in the quantitative analysis of total ionic iron. The multilayer element had the following structure:

| | Serum Total (Iron) Element Structure | | |
|---|---|---|---|
| | | \multicolumn{2}{c}{g/m²} |
| | | Preferred | Range |
| SPREAD LAYER | TiO₂ (Pigment) | 39 | 20–50 |
| | Estane 5715 (Binder) (available from B. F. Goodrich) | 2.5 | 0.5–5.0 |
| | Cellulose Acetate (Binder) | 7 | 5–15 |
| | Oleyl 10G } (Surfactants) | 0.8 | 0.1–3 |
| | TX-405 | 1.7 | 0.1–10 |
| REDUCING LAYER | Poly(vinyl pyrolidine) (Binder) | 6.0 | 1–12.0 |
| | Ascorbic Palimitate | 1.0 | 0.10–10.0 |
| | Neocuproine | 1.0 | 0.10–10.0 |
| REAGENT LAYER | DI V Gel (Binder) | 5 | 1–20 |
| | TX-100 (surfactant) (Rohm & Haas) | 0.6 | 0.1–3 |
| (Barrier Zone) | Bis(vinylsulfonylmethyl)-ether (Hardener) | 0.45 | 0.1–2 |
| | DI V Gel (Binder) | 10 | 2–30 |
| | Glutaric Acid (Buffer) | 4 | 0.5–10 |
| | TX-100 } (Surfactants) | 0.6 | 0.1–3 |
| (Reagent Zone) | Alkanol XC | 0.6 | 0.1–3 |
| | Dioctylphenyl Phosphonate (Coupler Solvent) | 3.0 | 0.5–8 |
| | Dye pH 4.5 | 0.3 | 0.01–2 |
| SUPPORT | Poly(ethylene terephthalate) | | |

EXAMPLE 1

Ferrous ion standard solutions were prepared in 1 mM HCl solution. Five minutes after 0.01 ml one of the standard solutions was contacted to the spreading layer of the above described element, colorimetric determination was carried out on a spectrophotometer. Reflection density readings on the elements were taken at 610 nm. Table I shows the results of these tests. The specific dye used was

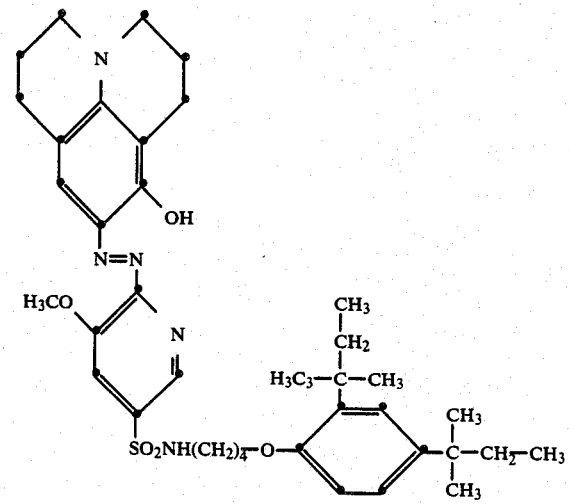

TABLE I

| Reference $Fe^{+2}$ Concentration mg/dl | No. of Tests | MEAN $D_R$ | Predicted Value | Precision Percent C.V. |
|---|---|---|---|---|
| 100 | 10 | 0.73910 | 91.14 | 10.01 |
| 200 | 10 | 0.76474 | 200.01 | 7.52 |
| 400 | 10 | 0.81634 | 394.50 | 2.45 |
| 600 | 10 | 0.86894 | 616.77 | 1.96 |
| 1000 | 10 | 0.95219 | 944.56 | 1.68 |

$D_R$ = mean reflectance density at 610 nm.
Predicted Values = concentration of $Fe^{+2}$ quantitatively determined using the method and elements of this invention.
C.V. = coefficient of variation from the arithmatical mean of all measurements in the series.

Table I shows that the $Fe^{+2}$ concentration, as determined using the method and element of this invention are in good agreement with the reference values for $Fe^{+2}$. The precision is also good.

COMPARATIVE EXAMPLE

The following example shows that, through the use of a coupler solvent, assay interferences by $Cu^{+2}$ and $Zn^{+2}$ are completely eliminated in the method and elements of this invention.

Aqueous solutions containing known amounts of $Fe^{+2}$, $Cu^{+2}$ and $Zn^{+2}$ prepared as described in the foregoing examples were tested according to the method of this invention using the multilayer elements used in the foregoing examples except one group of the element included a dye coating in the reagent layer according to the invention, 9-pyridylazo-8-hydroxyjulolidine. Another group included a prior art dye used for $Fe^{+2}$ ion determination. The dye was a ferrozine having the structure

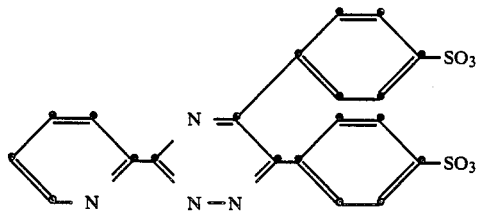

This dye is similar in structure to the dye disclosed for use in $Fe^{+2}$ analysis in *Clinical Chemistry*, Vol. 17, NO9, page 950, 1971.

Table II shows the results of these comparative tests for $Zn^{+2}$ and $Cu^{+2}$ ion interferences.

TABLE II

| Coating No. | Dye | Coupler Solvent | % Interference $Cu^{+2}$ | % Interference $Zn^{+2}$ |
|---|---|---|---|---|
| 1 | 9-pyridylazo-8-hydroxyjulolidine | 2,4-di-N—pentyl phenol | 0.12 | 57.0 |
| 2 | 9-pyridylazo-8-hydroxyjulolidine | diethyl lauramide | 0 | 0 |
| 3 | 9-pyridylazo-8-hydroxyjulolidine | dioctyl phosphonate | 0 | 0 |
| (Prior Art) | | | | |
| 1 | Ferrozine | 2,4-di-N—pentyl phenol | 0 | 5.1 |
| 2 | Ferrozine | diethyl lauramide | 0 | 9.4 |
| 3 | Ferrozine | dioctyl phosphonate | 0 | 0 |

It is apparent that the $Cu^{+2}$ and $Zn^{+2}$ sensitivity can be eliminated by the correct choice of coupler solvent. Not all coupler solvents are effective. This is shown in coating No. 1 in which the coupler solvent was 2,4-di-N-pentyl phenol. Those of the present invention have been carefully selected. The coupler solvents of the invention eliminated $Cu^{+2}$ ion interference with both dyes. The zinc interference was also eliminated with the dye ferrozine and the dyes of this invention. However, the extinction coefficient of ferrozine is insufficient to be of practical use in the elements of this invention.

The invention has been described in detail with particular reference to preferred embodiments thereof, but it will be understood that variations and modifications can be effected within the spirit and scope of the invention.

We claim:

1. A multilayer analytical element for quantitative determination of total ionic iron in an aqueous fluid comprising in the following order;
  (a) a spreading layer; and
  (b) a reducing layer comprising a reducing agent for $Fe^{+3}$; and
  (c) a reagent layer for complexing $Fe^{+2}$ iron comprising
    (i) a coupler solvent selected from the group consisting of dioctyl phenyl phosphonate and diethyl lauramide;
    (ii) a buffering composition of sufficient concentration to maintain a pH in the range of 4 to 5 when the reagent layer is contacted with an aqueous fluid and
    (iii) a dye having the structure

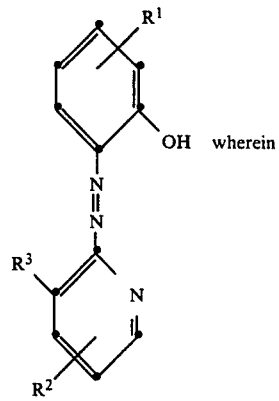

wherein $R^1$ represents an electron donating group; or $R^1$, together with the carbon to which it is attached, represents sufficient atoms to form a cyclic electron donating group fused to the phenyl group to which $R^1$ is attached;

$R^2$ represents an electron withdrawing group; and

R[3] represents H, Cl, F, Br or OR[4] wherein R[4] represents a hydrocarbon having from 1 to 20 carbon atoms.

2. The element of claim 1 wherein

R[1] represents dimethylamino or R[1] together with the phenyl group to which it is attached represents sufficient atoms to form a julolidyl fused ring structure;

R[2] represents

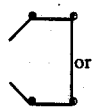

SO$_2$N(CH$_3$)$_2$, SO$_2$—N    or

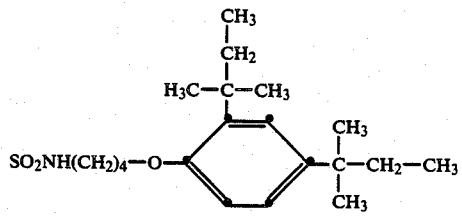

R[3] represents H or OCH$_3$.

3. The element of claim 1 wherein the dye is selected from the group consisting of

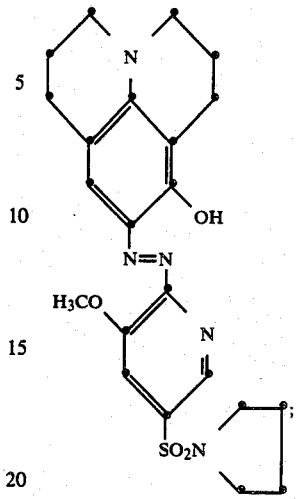

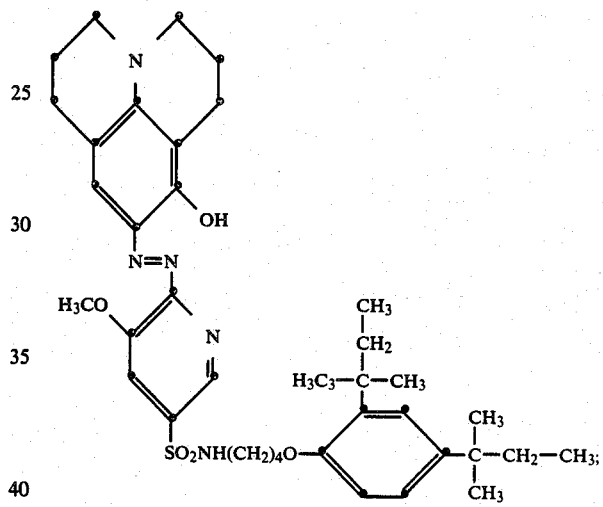

and

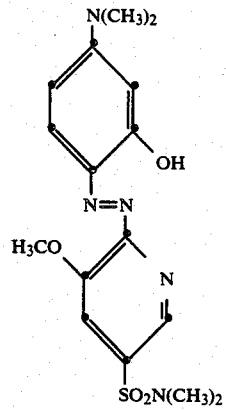

4. The element of claim 1 wherein the reagent layer further comprises a chelating material for copper and zinc ions and a barrier zone containing a gelatin and a gelatin hardener.

5. The element of claim 1 wherein neocuproine is included in the reducing layer or the reagent layer.

* * * * *